United States Patent [19]
Michelson et al.

[11] Patent Number: 5,552,290
[45] Date of Patent: Sep. 3, 1996

[54] DETECTION OF PROCOAGULANT PLATELET-DERIVED MICROPARTICLES IN WHOLE BLOOD

[75] Inventors: Alan D. Michelson, Sudbury; Marc. R. Barnard, Douglas, both of Mass.

[73] Assignee: University of Massachusetts Medical Center, Worcester, Mass.

[21] Appl. No.: 339,417

[22] Filed: Nov. 14, 1994

[51] Int. Cl.$^6$ .................................................. G01N 33/567
[52] U.S. Cl. ........................... 435/7.21; 435/13; 435/961; 435/962; 435/968; 436/519; 436/69; 436/172
[58] Field of Search ........................... 435/7.21, 13, 961, 435/962, 968; 436/519, 69, 172; 422/73; 424/532

[56] References Cited

U.S. PATENT DOCUMENTS

| | | | |
|---|---|---|---|
| 5,135,916 | 8/1992 | Sims et al. | 514/21 |
| 5,246,832 | 9/1993 | Michelson et al. | 435/7.2 |

OTHER PUBLICATIONS

C. Gemmell et al, "Platelet–Derived Microparticle Formation Involves Glycoprotein IIb–IIIa"in *J. of Biol. Chem.*268(20) 14586–14589, 1993.

Abrams et al., "Direct Detection of Activated Platelets and Platelet–Derived Microparticles in Human," *Blood*, 75:128–138 (1990).

Coller, "A New Murine Monoclonal Antibody Reports an Activation–dependent Change in the Conformation and/or Microenvironment of the Platelet Glycoprotein llb/llla Complex," *J. Clin. Invest.*, 76:101–108 (1985).

Dachary–Prigent et al.,"Annexin V as a Probe of Aminophospholipid Exposure and Platelet Membrane Vesiculation: A Flow Cytometry Study Showing a Role for Free Sulfhydryl Groups," *Blood*, 81:2554–65 (1993).

Gilbert et al.,"Platelet–derived Microparticles Express High Affinity Receptors for Factor VIII," *J. Biol. Chem.*, 266:17261–68 (1991).

Jy et al.,"Clinical Significance of Platelet Microparticles in Autoimmune Thrombocytopenias," *J. Lab. Clin. Med.*, 119:334–45 (1992).

Kestin et al.,"Effect of Strenuous Exercise on Platelet Activation State and Reactivity," *Circulation*, 88:1502–1511 (1993).

Michelson et al.,"Downregulation of the Platelet Surface Glycoprotein Ib–IX Complex in Whole Blood Stimulated by Thrombin, Adenosine Diphosphate, or an In Vivo Wound," *Blood*, 77:770–779 (1991).

Rajasekhar et al.,"Procoagulant Activity of Platelet–Derived Microparticles In Whole Blood: Differences Between Neonates and Adults," Blood, 82:163a (1993) (Abstract).

Shattil et al.,"Detection of Activated Platelets in Whole Blood Using Activation–Dependent Monoclonal Antibodies and Flow Cytometry," *Blood*, 70:307–315 (1987).

Shattil et al.,"Changes in the Platelet Membrane Glycoprotein IIb IIIa Complex during Platelet Activation," *J. Biol. Chem.*, 260:11107–14, (1985).

Sims et al.,"Complement Proteins C5b–9 Cause Release of Membrane Vesicles from the Platelet Surface That Are Enriched in the Membrane Receptor for Coagulation Factor Va and Express Prothrombinase Activity," *J. Biol. Chem.*, 263: 18205–18212 (1988).

Zwall et al., "Platelet Procoagulant Activity and Microvesicle Formation. Its Putative Role in Hemostasis and Thrombosis", (1992) Biochimica et Biophysica Acta, 1180, 1–8.

Sims et al., "Assembly of the Platelet Prothrombinase Complex is Linked to Vesiculation of the Platelet Plasma Membrane", (1989) The Journal of Biological Chemistry, vol. 264, No. 29, 17049–17057.

Bode et al., "Vesiculation of Platelets During in Vitro Aging", (1991) Blood, vol. 77, No. 4, 887–895.

Hoffman et al., "Coagulation Factor IXa Binding to Activated Platelets and Platelet–derived Microparticles: a Flow Cytometric Study", (1992), 74–78.

George et al., "Isolation of Human Platelet Membrane Microparticles from Plasma and Serum", (1982) Blood, vol. 60, No. 4, 834–840.

Lee et al.,"Elevated Platelet Microparticles in Transient Isohemic Attacks, Lacunar Infarcts, and Multiinfarct Dementias", (1993) Platelet Particles in Ischemia, vol. 72, No. 4, 295–304.

Zucker–Franklin et al.,"Red–Cell and Platelet Fragmentation in Idiopathic Autoimmune Thrombocytopenic Purpura", (1977) The New England Journal of Medicine, vol. 297, No. 10, 517–523.

*Primary Examiner*—Carol A. Spiegel
*Attorney, Agent, or Firm*—Fish & Richardson P.C.

[57] ABSTRACT

A flow cytometric method for determining procoagulant platelet-derived microparticles in whole blood is described. The invention also provides a method for measuring platelet reactivity in whole blood by measurement of PDMP generated *in vitro* in the presence of an inhibitor of fibrin clot formation.

27 Claims, No Drawings

DETECTION OF PROCOAGULANT PLATELET-DERIVED MICROPARTICLES IN WHOLE BLOOD

BACKGROUND OF THE INVENTION

This invention relates to blood platelets and assays for determining platelet activation.

Upon activation, human platelets undergo changes in platelet surface membrane receptors, which may result in platelet aggregation, interaction with fibrin fibers, and the resulting formation of a thrombus. In certain disease states, e.g., coronary artery disease and diabetes, platelets may exist in a hyperreactive state, resulting in increased risk to the patient of thrombosis. Early detection of platelet hyperreactivity can permit the timely administration of antiplatelet drugs. Platelets may also exist in a hyporeactive state, placing a patient at risk of hemorrhage.

α-thrombin is among the most physiologically important activators of platelets. Quantitative determination of thrombin-induced changes in specific receptors, as measured by monoclonal antibody binding, has been carried out in assays performed on washed and resuspended platelets. Activation of platelets by adenosine diphosphate (ADP) and epinephrine has been measured in a whole blood assay by flow cytometry (Shattil et al. (1987) Blood 70:307–315).

It is known that the tetrapeptide glycyl-L-prolyl-L-arginyl-L-proline (GPRP), an analog of the amino terminus of the α-chain of fibrinogen and the fibrin monomer, binds to fibrinogen and, under some experimental conditions, inhibits fibrin polymerization.

U.S. Pat. No. 5,246,832 (issued September 21, 1993 to Michelson et al.) describes a method for measuring the thrombin reactivity of activated platelets in whole blood by flow cytometry. Total platelets are identified using an antiplatelet antibody labeled with a first fluorophore emitting light at a given wavelength. α-thrombin-activated platelets are then identified using a second, activated platelet-specific antibody labeled with a second fluorophore emitting light at a second, different wavelength. Thrombin-induced fibrin clot formation is inhibited by inclusion in the assay of GPRP (Michelson et al. (1991) Blood 77:770–779; Kestin et al. (1993) Circulation 88:1502–1511).

Platelet activation results in the shedding of small fragments of platelets, termed platelet-derived microparticles (PDMP). The surface of these PDMP provide the primary procoagulant surface, i.e., they are critical for the promotion of blood clotting. For example, PDMP bind coagulant factors V and VIII more avidly than platelets. PDMP appear to have a major role in the generation of procoagulant activity and, therefore, detection of PDMP is a useful indicator of procoagulant status (Sims et al. (1988) J. Biol. Chem. 263:18205–18212; Gilbert et al. (1991) J. Biol. Chem. 266:17261–17268). PDMP have been counted in a washed platelet system (Jy et al. (1992) J. Lab. Clin. Med. 119:334–345). Sims et al. (1988) supra and Gilbert et al. (1991) supra demonstrated that PDMP bind coagulant factors V and VIII, i.e., PDMP are procoagulant in a washed platelet system.

Prior art measurement of PDMP in whole blood (Abrams (1990) Blood 75:128–138) did not allow evaluation of the ability of platelets to generate PDMP *in vitro* in response to an agonist, because the addition of sufficient $Ca^{++}$ for PDMP formation also results in stimulation of fibrin clot formation.

SUMMARY OF THE INVENTION

The present invention allows, for the first time, measurement of procoagulant PDMP in whole blood, and evaluation of the ability of platelets to generate procoagulant PDMP in whole blood *in vitro* in response to an agonist.

Accordingly, the invention features a method for detecting procoagulant platelet-derived microparticles (PDMP) in whole blood, involving identifying total platelets using a first platelet-specific labeled agent and identifying procoagulant PDMP with a second agent specific for procoagulant PDMP.

By the term "platelet-specific agent" is meant an agent which specifically identifies platelets, for example, antibodies directed to a platelet-specific surface antigen.

By the term "specific for procoagulant PDMP" is meant an agent able to identify procoagulant PDMP, either by binding a coagulant factor bound by PDMP or by binding directly to procoagulant PDMP. Procoagulant PDMP-specific agents include antibodies to a coagulant factor or proteins such as annexin V (Dachary-Prigent et al. (1993) Blood 81:2554–2565.

In one aspect, a method is provided for detecting *in vivo* PDMP in whole blood, involving obtaining a sample of whole blood from a patient, adding an inhibitor of fibrin clot formation, adding a first platelet-specific agent to the sample which binds platelets, adding a second agent to the sample which specifically identifies procoagulant PDMP, and detecting sample-bound first and second agents as indicators of PDMP. In specific embodiments of the invention, the platelet-specific agent is an antibody directed to a platelet-specific antigen, such as GPIb or GPIIb-IIIa, and the procoagulant PDMP-specific agent is a coagulant factor, such as coagulant factor II, V, VIII, or X, or a protein, such as annexin V.

In a related aspect, the invention provides a method of determining platelet reactivity in whole blood by *in vitro* generation of PDMP involving obtaining a sample of whole blood from a patient, generating PDMP *in vitro* in the presence of an inhibitor of fibrin clot formation, and using flow cytometry to identify procoagulant PDMP by PDMP binding of a first platelet-specific agent and of a second agent specific for procoagulant PDMP.

In the methods of the invention, blood samples obtained from a patient are treated with an anticoagulant to inhibit blood clot formation. Preferably, the anticoagulant is sodium citrate.

In an embodiment, autologous plasma is added to the blood sample to provide an adequate concentration of coagulation factors. By the term "autologous plasma" is meant plasma from the same individual from which the blood was drawn.

The methods of the invention include the addition of an inhibitor of fibrin clot formation or polymerization to the whole blood sample. Preferably, the agent which inhibits fibrin polymerization does so by competitive inhibition. A particular class of molecules are those capable of binding to fibrinogen and fibrin monomer to inhibit fibrin[ogen]-fibrin [ogen] interactions which otherwise would lead to clot formation. Such inhibitory agents include molecules which mimic, in their fibrinogen binding property, the action of the amino terminal half of native human fibrinogen. Particular such agents are peptides, preferably those containing between two and twenty amino acid residues, and more preferably peptides containing between four and ten amino acid residues. It is preferred that the peptide have at least 75% homology, and more preferably, 100% homology with a region contained in the amino terminal half of native human fibrinogen. The currently most preferred inhibitory peptide is the tetrapeptide glycyl-L-prolyl-L-arginyl-L-proline (GPRP). Another suitable inhibitory agent is an antibody capable of binding to the amino terminal half of native human fibrinogen.

PDMP may be generated *in vitro* in a whole blood sample by a variety of methods. For example, $CaCl_2$ can be added to whole blood to generate PDMP. Alternatively, PDMP can also be generated by the addition of $CaCl_2$ and a calcium ionophore such as A23187. In another aspect, PDMP are generated by the addition of $CaCl_2$, $\alpha$-thrombin and collagen. Other agents may be used to generate PDMP, for example, $CaCl_2$ plus adenosine diphosphate and epinephrine, or complement proteins C5b-9.

Methods for the detection of PDMP in washed platelet systems (Jy et al. (1992) supra; Sims et al. (1988) supra) require separation of the platelets from whole blood by washing or other means. These separation processes can result in artifactual platelet activation with the release of PDMP. Artifactual platelet activation presents a particular problem in the pathological setting of platelet hyperreactivity (e.g., coronary artery disease) in which a PDMP assay has particular clinical relevance.

Because of the methodological problems of plasma and washed platelet assays, there are currently very few clinically useful assays of platelet activation. Prior to the present invention, there were no methods available for measurement of procoagulant PDMP in whole blood. The present invention provides a method of detecting PDMP in the more physiological milieu of whole blood that does not suffer from the artifactual problems associated with currently available washed platelet methods.

The method of the present invention is clinically useful because platelet activation and the release of PDMP may occur in a large number of conditions, e.g., coronary artery disease (including angina pectoris and acute myocardial infarction), diabetes mellitus, stroke, exercise stress, emotional stress, cigarette smoking, pregnancy and pre-eclampsia, blood bank storage of platelets for transfusion, cardiopulmonary bypass, angioplasty, deep vein thrombosis, hyperlipoproteinemia, essential thrombocythemia, and adult respiratory distress syndrome. The present invention has the additional advantage of requiring only about 5 µl of blood per assay.

Other features and advantages of the invention will be apparent from the following description of the preferred embodiments thereof, and from the claims.

DETAILED DESCRIPTION

The invention features a method for detecting procoagulant platelet-derived microparticles (PDMP) in whole blood. PDMP are small fragments of platelets which are shed upon activation of platelets. The surface of these PDMP promote blood clotting, that is, they are procoagulant. For example, PDMP bind coagulation factors V and VIII more avidly than platelets. Thus, PDMP appear to play a major role in the generation of procoagulant activity. However, not all PDMP are procoagulant. As shown by the inventors in Example 2 below, PDMP from preterm neonates exhibited markedly less procoagulant activity.

In the present invention, procoagulant PDMP are analyzed directly in whole blood. This method is widely applicable for use in many clinical settings, since platelet activation and the release of PDMP may occur in a large number of clinical settings. The invention is particularly well suited for clinical use because only 5 µl of blood are required per assay.

The flow cytometric method for determination of PDMP is described in Example 1. Platelet reactivity was determined by *in vitro* generation of PDMP in whole blood samples obtained from preterm neonates, term neonates, and adults (Example 2). There were no significant differences between the groups in the number of PDMP formed in response to $CaCl_2$ alone or $CaCl_2$ with thrombin; however, both groups of neonates formed significantly more PDMP in response to $CaCl_2$ with a calcium ionophore. Compared to adult controls, PDMP of preterm neonates bound markedly less coagulation factor V, reflecting reduced procoagulant activity. The fact that adult plasma did not fully correct the marked procoagulant defect in PDMP of preterm neonates suggested that part of the defect was intrinsic to the platelets. The marked procoagulant defect in PDMP of preterm neonates may contribute to the propensity of these infants to hemorrhage.

Example 3 describes the use of the present method to measure *in vivo* procoagulant PDMP in patients with coronary heart disease. Based on the known role of platelet activation in coronary artery thrombosis and restenosis after angioplasty, the method of the invention is useful in identifying patients at risk for complications such as acute myocardial infarction and restenosis.

EXAMPLE 1

Flow cytometric assay for PDMP.

Assay steps. The detection of PDMP in whole blood according to the method of the invention involves inhibition of platelet aggregation and fibrin clotting using a peptide such as the tetrapeptide glycyl-L-propyl-L-arginyl-L-proline (GPRP). To a blood sample from a patient from which PDMP is to be determined is added GPRP and autologous plasma. PDMP may be generated by a number of methods, including by the addition of $CaCl_2$ alone, or $CaCl_2$ with thrombin and collagen, or $CaCl_{12}$ with a calcium ionophore such as A23187.

Monoclonal antibodies used. Two murine monoclonal antibodies (6D1 and V237) were used to identify procoagulant PDMP. Phycoerythrin-labeled GPIb-specific monoclonal antibody 6D1 (provided by Dr. Barry S. Coller, Mount Sinai Medical Center, NY) is directed against the von Willebrand factor receptor on the glycocalicin portion of the $\alpha$-chain of platelet membrane GPIb. Fluorescein-conjugated monoclonal antibody V237 (provided by Dr. C. Esmon, Oklahoma Medical Research Foundation) is directed against coagulation factor V.

Blood sample preparation. To minimize artifactual formation of PDMP, PDMP was measured by flow cytometry without separation of platelets and/or PDMP from whole blood. Blood samples (0.5 ml) were drawn by venipuncture from normal subjects into sodium citrate anticoagulant (10:1 dilution). To minimize platelet activation during blood drawing, only a light tourniquet and a 19 gauge needle was used, and the first 2 ml of blood discarded. Preparation of the blood samples was designed to avoid the formation of platelet aggregates, using a modified version of the method of Michelson et al. (1991) Blood 77:770–779. Thus, in the preparation of whole blood for platelet analysis, there is no washing, centrifugation, gel filtration, vortexing, or stirring steps. A separate aliquot of 300 µl of blood was centrifuged for 2 min to prepare autologous plasma.

Each 24 µl of the citrated whole blood sample were treated as follows:

(1) 2.5 mM of gly-pro-arg-pro (Calbiochem, San Diego) was added to inhibit fibrin polymerization and platelet aggregation;

(2) autologous plasma was added (final concentration 20%) to provide adequate concentrations of coagulation factors;

(3) a saturating concentration of biotinylated monoclonal antibody 6D1 (GPIb-specific) was added and the sample incubated for 10 min at 22° C.;

(4) one of the following agonists was added and the sample incubated for 10 min at 37° C.: (a) thrombin (2 U/ml) (provided by John W. Fenton, II, New York Department of Health, Albany)+CaCl$_2$ (3 mM); (b) ADP (20 μM)+epinephrine (20 μM)+CaCl$_2$ (3 mM); (c) calcium ionophore A23187+CaCl$_2$ (3 mM); (d) CaCl$_2$ (3 mM); or (e) buffer only;

(5) phycoerythrin streptavidin and either a saturating concentration of fluorescein-conjugated monoclonal antibody V237 (factor V-specific) or fluorescein-conjugated mouse IgG isotypic (control) were added, with incubation of the sample for 15 min at 22° C.;

(6) 1% formaldehyde was added with incubation for 20 min at 22° C.; and (7) the sample was diluted 25-fold with HEPES-Tyrode's buffer (pH 7.4).

Sample analysis. Samples are analyzed in an EPICS Profile flow cytometer (Coulter Cytometry, Hialeah, Fla.) equipped with a 100 mW argon laser and operated at 15 mW power at a wavelength of 488 nm. The fluorescence of phycoerythrin and fluorescein are detected using 575 nm and 525 nm band pass filters, respectively. Flow cytometry was used to identify procoagulant PDMP in whole blood by: log forward light scatter less than 0.7 μm standardized beads, binding of the labeled GPIb-specific monoclonal antibody (6D1), and binding of the labeled coagulation factor V antibody (V237).

EXAMPLE 2

Determination of PDMP in whole blood from adults, term neonates, and preterm neonates.

Peripheral blood samples were collected from 7 term neonates (38–41 weeks gestation), 8 preterm neonates (24–30 weeks gestation), and 13 adult controls as described above.

PDMP were generated by addition of (1) 3 mM CaCl$_2$, (2) 3 mM CaCl$_2$ with 2 U/ml human α-thrombin and 20 μg/ml collagen, or (3) 3 mM CaCl$_2$ with 20 μM calcium ionophore A23187.

There were no significant differences between preterm, term and adult platelets in the number of PDMP formed in response to CaCl$_2$ and CaCl$_2$/thrombin/collagen. In response to CaCl$_2$/A23187, platelets of term and preterm neonates formed 34.5±7.0% (mean±SEM) and 38.2±6.2% more PDMP than adult platelets. In term neonates, CaCl$_2$/A23187-induced binding of coagulation factor V to PDMP (as determined by V237) was 90.1±9.6% of adults. In preterm neonates, CaCl$_2$/A23187-induced binding of factor V to PDMP was only 36.9 ±11.5% of adults; this increased to 70.5±17.5% when adult plasma was added. Similar results were obtained when either CaCl$_2$/thrombin/collagen or CaCl$_2$ alone were used rather than CaCl$_2$/A23187.

EXAMPLE 3

Determination of PDMP in patients with coronary heart disease.

Blood samples are obtained either from a peripheral vein or from the coronary artery via catheter from adults with coronary artery disease in order to determine the number of circulating procoagulant PDMP, and to determine the reactivity of platelets as determined by the *in vitro* generation of procoagulant PDMP.

PDMP are generated by addition of 3 mM CaCl$_2$, with or without calcium ionophore A23187 or 2 U/ml human α-thrombin plus 20 μg/ml collagen.

Other embodiments.

Other embodiments are within the following claims. For example, any analogue of GPRP that prevents the polymerization of fibrin monomers can be used to block fibrin clot formation in the whole blood assay. Other methods of detecting PDMP generation could be employed in addition to flow cytometry, such as radio-immunoassay, enzyme-linked immunoassay, magnetic bead cell separation, or microscopy.

What is claimed is:

1. A method for detecting procoagulant platelet-derived microparticles in whole blood comprising:

a) obtaining an anticoagulated sample of said whole blood from a patient;

b) contacting said sample with an inhibitor of fibrin clot formation, wherein said inhibitor is selected from the group consisting of (i) glycyl-L-prolyl-L-arginyl-L-proline, (ii) molecules having 2–20 amino acides of the amino terminal half of human fibrinogen, and (iii) an antibody which specifically binds to the amino terminal half of said human fibrinogen;

c) contacting said sample of step b) with a first agent comprising a first detectable label, under conditions whereby said first labeled agent specifically binds to any platelets and any PDMP to identify said platelets and said PDMP;

d) contacting said sample of step c) with a second agent comprising a second detectable label, under conditions whereby said second labeled agent specifically binds to any procoagulant PDMP to distinguish said procoagulant PDMP from said platelets and any non-procoagulant PDMP, wherein said first and second labels are different; and e) detecting said procoagulant PDMP by detecting any PDMP which are specifically bound by both said first labeled agent and said second labeled agent.

2. The method of claim 1, wherein the labels are fluorescence emitting labels.

3. The method of claim 1, wherein the agents are detected by flow cytometry.

4. The method of claim 1, wherein said first agent is a platelet-specific antibody which specifically binds a surface antigen of a platelet.

5. The method of claim 4, wherein said antibody specifically binds surface antigen GPIb.

6. The method of claim 4, wherein said antibody specifically binds surface antigen GPIIb-IIIa.

7. The method of claim 1, wherein said second agent is a protein.

8. The method of claim 7, wherein said protein is annexin V.

9. The method of claim 1, wherein said second agent is an antibody which specifically binds a coagulation factor bound by said procoagulant PDMP.

10. The method of claim 9, wherein said antibody specifically binds coagulant factor II, V, VIII, or X.

11. The method of claim 1 further comprising adding autologous plasma to the sample between steps b) and c).

12. A method of detecting abnormal platelet reactivity in a patient by detecting procoagulant platelet-derived microparticles (PDMP) in whole blood from said patient, comprising:

a) obtaining an anticoagulated sample of said whole blood from said patient;

b) contacting said sample with an inhibitor of fibrin clot formation, wherein said inhibitor is selected from the group consisting of (i) glycyl-L-prolyl-L-arginyl-L-proline, (ii) molecules having 2–20 amino acides of the amino terminal half of human fibrinogen, and (iii) an antibody which specifically binds to the amino terminal half of said human fibrinogen;

c) generating said procoagulant PDMP in said sample of step b);

d) contacting said sample of step c) with a first agent comprising a first detectable label, under conditions whereby said first labeled agent specifically binds to any platelets and any PDMP to identify said platelets and said PDMP;

e) contacting said sample of step d) with a second agent comprising a second detectable label, under conditions whereby said second labeled agent specifically binds to any procoagulant PDMP to distinguish said procoagulant PDMP from said platelets and any non-procoagulant PDMP, wherein said first and second labels are different;

f) detecting said procoagulant PDMP in said sample of whole blood from said patient by detecting any PDMP which are specifically bound by both said first labeled agent and said second labeled agent;

g) repeating steps a) through f) using whole blood from a normal control; and h) comparing said procoagulant PDMP in said patient to said procoagulant PDMP in said normal control to detect abnormal platelet reactivity in said patient.

13. The method of claim 12, wherein the labels are fluorescence emitting labels.

14. The method of claim 12, wherein the agents are detected by flow cytometry.

15. The method of claim 12, wherein said first agent is a platelet-specific antibody which specifically binds a surface antigen of a platelet.

16. The method of claim 15, wherein said antibody specifically binds surface antigen GPIb.

17. The method of claim 15, wherein said antibody specifically binds surface antigen GPIIb-IIIa.

18. The method of claim 12, wherein said second agent is a protein.

19. The method of claim 18, wherein said protein is annexin V.

20. The method of claim 12, wherein said second agent is an antibody which specifically binds a coagulation factor bound by said procoagulant PDMP.

21. The method of claim 20, wherein said antibody specifically binds coagulant factor II, V, VIII, or X.

22. The method of claim 12 further comprising adding autologous plasma to the sample between steps b) and c).

23. The method of claim 12, wherein said procoagulant PDMP is generated by addition of $CaCl_2$.

24. The method of claim 12, wherein said procoagulant PDMP is generated by addition of a calcium ionophore or human α-thrombin plus collagen.

25. The method of claim 24, wherein the calcium ionophore is A23187.

26. The method of claim 12, wherein said procoagulant PDMP is generated by addition of complement proteins C5b-9.

27. The method of claim 12, wherein said procoagulant PDMP is generated by addition of adenosine diphosphate plus epinephrine.

* * * * *

UNITED STATES PATENT AND TRADEMARK OFFICE
CERTIFICATE OF CORRECTION

PATENT NO. : 5,552,290

DATED : September 3, 1996

INVENTOR(S) : Alan D. Michelson et al.

It is certified that error appears in the above-identified patent and that said Letters Patent is hereby corrected as shown below:

Col. 4, line 36, after "or" delete "$CaCl_{12}$" and insert therefor --$CaCl_2$--;

Claim 1, Col. 6, line 18, after "microparticles", insert --(PDMP)--; and

Claim 1, Col. 6, line 24, delete "acides" and insert therefor --acids--.

Signed and Sealed this

Twenty-sixth Day of May, 1998

BRUCE LEHMAN

Attest:

Attesting Officer

Commissioner of Patents and Trademarks